(12) United States Patent
Luithle et al.

(10) Patent No.: US 9,914,729 B2
(45) Date of Patent: *Mar. 13, 2018

(54) AMIDES OF ACETIC AND PROPIONIC ACIDS

(71) Applicant: BAYER INTELLECTUAL PROPERTY GMBH, Monheim (DE)

(72) Inventors: Joachim Luithle, Wulfrath (DE);
Frank-Gerhard BÖβ, Sunninghill (GB); Christina Erb, Wiesbaden (DE);
Katrin Schnizler, Rodenbach (DE);
Timo Flessner, Wuppertal (DE); Marja van Kampen, Neu-Isenburg (DE);
Christoph Methfessel, Wuppertal (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/229,561

(22) Filed: Aug. 5, 2016

(65) Prior Publication Data

US 2017/0183339 A1    Jun. 29, 2017

Related U.S. Application Data

(63) Continuation of application No. 14/633,985, filed on Feb. 27, 2015, now Pat. No. 9,433,614, which is a continuation of application No. 13/968,536, filed on Aug. 16, 2013, now Pat. No. 9,000,008, which is a continuation of application No. 12/494,009, filed on Jun. 29, 2009, now Pat. No. 8,518,967, which is a continuation of application No. 10/508,106, filed as application No. PCT/EP03/02152 on Mar. 3, 2003, now Pat. No. 7,553,851.

(30) Foreign Application Priority Data

Mar. 15, 2002 (DE) .................. 102 11 416

(51) Int. Cl.
C07D 453/02 (2006.01)

(52) U.S. Cl.
CPC ................ *C07D 453/02* (2013.01)

(58) Field of Classification Search
None
See application file for complete search history.

(56) References Cited

U.S. PATENT DOCUMENTS

| | | | |
|---|---|---|---|
| 5,852,038 A | 12/1998 | Ito et al. | |
| 7,553,851 B2 | 6/2009 | Luithle et al. | |
| 8,518,967 B2 | 8/2013 | Luithle et al. | |
| 9,000,008 B2 * | 4/2015 | Luithle | C07D 453/02 514/305 |
| 9,433,614 B2 * | 9/2016 | Luithle | C07D 453/02 |

FOREIGN PATENT DOCUMENTS

| | | |
|---|---|---|
| FR | 1566045 A | 5/1969 |
| GB | 1578421 A | 11/1980 |
| WO | WO-2001/02405 A1 | 1/2001 |
| WO | WO-2001/60821 A1 | 8/2001 |

OTHER PUBLICATIONS

J-L. Galzi et al.: "Neuronal Nicotinic Receptors: Molecular Organization and Regulations," Neuropharmacology, vol. 34, No. 6, 1995, pp. 563-582.
D. S. McGehee et al.: "Physiological Diversity of Nicotinic Acetylcholine Receptors Expressed by Vertebrate Neurons," Annu. Rev. Physiol., vol. 57, 1995, pp. 521-546.
A. H. Rezvani et al.: "Cognitive Effects of Nicotine," Biological Pshychiatry, vol. 49, 2001, pp. 258-267.
P. Seguela et al.: "Molecular Cloning, Functional Properties, and Distribution of Rat Brain $\alpha_7$: A Nicotinic Cation Channel Highly Permeable to Calcium," The Journal fo Neuroscience, vol. 13, No. 2, Feb. 1993, pp. 596-604.
R. S. Broide et al.: "The $\alpha 7$ Nicotinic Acetylcholine Receptor in Neuronal Plasticity," Molecular Neurobiology, vol. 20, 1999, pp. 1-16.
E. Oppenheimer et al.: "EO-1999, A Specific Antagonist of Antiarrhythmic Drugs: Assessment by Binding Experiments and In Vivo Studies," Life Sciences, vol. 48, 1991, pp. 977-985.
A. R. West et al.: "Solid State Chem. and its Appl.," Wiley, New York, 1988, pp. 358 & 365.
A. Ennaceur et al.: "Effects of Physostigmine and Scopolamine on Rats' Performances in Object Recognition and Radial-Maze Tests," Pshychopharmacology, vol. 109, 1992, pp. 321-330.
E. Ennaceur et al.: "A New One-Trial Test for Neurobiological Studies of Memory in Rats. 1: Behavorial Data," Behavioural Brain Research, vol. 31, 1988, pp. 47-59.
A. Blokland et al.: "State-Dependent Impairment in Object Recognition after Hippocampal NOS Inhibition," NeuroReport, vol. 9, 1998, pp. 4205-42058.
M. Kato et al.: "New 5--HT$_3$-(Serotonin-3) Receptor Antagonists. IV. Synthesis and Structure-Activity Relationships of Azabicycloalkaneacetaide Derivatives," Chem. Phar. Bull, vol. 43, No. 8, 1995, pp. 1351-1357.
A. R. L. Davies et al.: "Charaterisation of the Binding of [$^3$H]methyllycaconitine: a New Radioligand for Labelling $\alpha 7$-type Neuronal Nicotinic Acetylcholine Receptors," Neuropharmacology, vol. 38, 1999, pp. 679-690.
J. Prickaerts et al.: "Possible Role of Nitric Oxide-Cyclic GMP Pathway in Object Recognition Memory: Effects of 7-Nitroindazole and Zaprinast," European Journal of Pharmacology, vol. 337, 1997-, pp. 125-136.
A. Blodland et al.: "State-Dependent Impairment in Object Recognition after Hippocampal NOS Inhibition," NeuroReport, vol. 9, 1998, pp. 4205-42058.

* cited by examiner

*Primary Examiner* — Zinna Northington Davis
(74) *Attorney, Agent, or Firm* — Morrison & Foerster LLP

(57) ABSTRACT

The invention relates to novel amides of acetic and propionic acids, methods for production and use thereof for the production of medicaments for the treatment and/or prophylaxis of diseases and for improving perception, concentration, learning ability and memory.

12 Claims, No Drawings

AMIDES OF ACETIC AND PROPIONIC ACIDS

CROSS REFERENCE TO RELATED APPLICATIONS

This application is a continuation of U.S. patent application Ser. No. 14/633,985, filed Feb. 27, 2015, which application is a continuation of U.S. patent application Ser. No. 13/968,536, filed Aug. 16, 2013, now U.S. Pat. No. 9,000,008, which application is a continuation of U.S. patent application Ser. No. 12/494,009, filed Jun. 29, 2009, now U.S. Pat. No. 8,518,967, which application is a continuation of U.S. patent application Ser. No. 10/508,106 filed May 6, 2005, now U.S. Pat. No. 7,553,851, which is the U.S. National Stage application under 35 U.S.C. §371 of International Patent Application Serial No. PCT/EP03/02152, filed Mar. 3, 2003, which claims the benefit of German Patent Application No. 102 11 416.1, filed Mar. 15, 2002, the disclosures of each of which are expressly incorporated by reference in their entireties.

The invention relates to novel amides of acetic and propionic acids, to a process for the preparation thereof and to the use thereof for producing medicaments for the treatment and/or prophylaxis of diseases and for improving perception, concentration, learning and/or memory.

Nicotinic acetylcholine receptors (nAChR) form a large family of ion channels which are activated by the messenger acetylcholine which is produced in the body (Galzi and Changeux, *Neuropharmacol.* 1995, 34, 563-582). A functional nAChR consists of five subunits which may be different (certain combinations of α1-9 and β1-4,γ,δ,ε subunits) or identical (α7-9). This leads to the formation of a diversity of subtypes which differ in the distribution in the muscles the nervous system and other organs (McGehee and Role, *Annu. Rev. Physiol.* 1995, 57, 521-546). Activation of nAChR, leads to influx of cations into the cell and to stimulation of nerve cells or muscle cells. Selective activation of individual nAChR subtypes restricts this stimulation to the cell types which have the corresponding subtype and is thus able to avoid unwanted side effects such as, for example, stimulation of nAChR in the muscles. Clinical experiments with nicotine and experiments in various animal models indicate that central nicotinic acetylchloline receptors are involved in learning and memory processes (e.g. Rezvani and Levin, *Biol. Psychiatry* 2001, 49, 258-267). Nicotinic acetylcholine receptors of the alpha7 subtype (α7 nAChR) have a particularly high concentration in regions of the brain which are important for learning and memory, such as the hippocampus and the cerebral cortex (Séguéla et al., *J. Neurosci.* 1993, 13, 596-604): The α7 nAChR has a particularly high permeability for calcium ions, increases glutamatergic neurotransmission, influences the growth of axons and, in this way, modulates neuronal plasticity (Broide and Leslie, *Mol. Neurobiol.* 1999, 20, 1-16).

Certain quinuclidinecarboxanilides are described as antiarrhythmics and local anesthetics (cf., for example, FR 1.566.045, GB 1 578 421 and Oppenheimer et al. *Life Sci.* 1991, 48, 977-985).

WO 01/60821 discloses biarylcarboxamides with affinity for the α7 nAChR for the treatment of learning and perception impairments.

The present invention relates to compounds of the general formula (I)

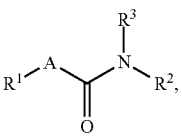

in which
R$^1$ is a 1-azabicyclo[m.n.p]alkyl radical having 7 to 11 ring atoms,
    in which m and n are independently of one another 2 or 3,
    in which p is 1, 2 or 3,
    and where the bicycloalkyl radical is optionally substituted by (C$_1$-C$_6$)-alkyl,
A is methylene or ethylene,
R$^2$ 8- to 10-membered heteroaryl, naphthyl or azulenyl, where the rings are optionally substituted by radicals selected from the group of halogen, formyl, —CO—NR$^4$R$^5$, —CO—OR$^6$, —NR$^7$R$^8$, —NR$^9$—CO—R$^{10}$, cyano, trifluoromethyl, trifluoromethoxy, nitro, optionally hydroxyl-, amino-, —NH—CO—R$^{11}$— or cyano-substituted (C$_1$-C$_6$)-alkyl, (C$_1$-C$_6$)-alkoxy, (C$_1$-C$_6$)-alkylthio, in which R$^4$, R$^5$, R$^6$, R$^7$, R$^8$, R$^9$, R$^{10}$ and R$^{11}$ are independently of one another hydrogen, (C$_1$-C$_6$)-alkyl, phenyl or benzyl,
and
R$^3$ is hydrogen or (C$_1$-C$_6$)-alkyl.

The compounds of the invention may exist in stereoisomeric forms which either are related as image and mirror image (enantiomers) or which are not related as image and mirror image (diastereomers). The invention relates both to the enantiomers or diastereomers or respective mixtures thereof. These mixtures are enantiomers and diastereomers which can be separated in a known manner into the stereoisomerically pure constituents.

The compounds of the invention may also be in the form of their salts, solvates or solvates of the salts.

Salts which are preferred for the purposes of the invention are physiologically acceptable salts of the compounds of the invention.

Physiologically acceptable salts of the compounds of the invention may be acid addition salts of the compounds with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

However, salts which may be mentioned are also salts with conventional bases, such as, for example, alkali metal salts (e.g. sodium or potassium salts), alkaline earth metal salts (e.g. Calcium or magnesium salts) or ammonium salts derived from ammonia or organic amines such as, for example, diethylamine, triethylamine, ethyldiisopropylamine, procaine, dibenzylamine, N-methylmorpholine, dihydro-abietylamine, 1-ephenamine or N-methylpiperidine.

Solvates is the term used for the purposes of the invention for those forms of the compounds which form a complex with solvent molecules by coordination in the solid or liquid state. Hydrates are a special form of solvates in which the coordination takes place with water.

For the purposes of the present invention, the substituents generally have the following meaning:

$(C_1-C_6)$- and $(C_1-C_4)$-alkoxy stands for a Straight-chain or branched alkoxy radical respectively having 1 to 6 and 1 to 4 carbon atoms. Preference is given to a straight-chain or branched alkoxy radical having 1 to 4, particularly preferably having 1 to 3, carbon atoms. The following may be mentioned by way of example and preferably: methoxy, ethoxy, n-propoxy, isopropoxy, tert-butoxy, n-pentoxy and n-hexoxy.

$(C_1-C_6)$— and $(C_1-C_4)$-alkyl stand for a straight-chain or branched alkyl radical respectively having 1 to 6 and 1 to 4 carbon atoms. Preference is given to a straight-chain or branched alkyl radical having 1 to 4, particularly preferably having 1 to 3, carbon atoms. The following may be mentioned by way of example and preferably: methyl, ethyl, n-propyl, isopropyl, tert-butyl, n-pentyl and n-hexyl.

$(C_1-C_6)$-Alkylthio stands for a straight-chain or branched alkylthio radical having 1 to 6 carbon atoms. Preference is given to a straight-chain or branched alkylthio radical having 1 to 4, particularly preferably having 1 to 3, carbon atoms. The following may be mentioned by way of example and preferably: methylthio, ethylthio, n-propylthio, isopropylthio, tert-butylthio, n-pentylthio and n-hexylthio.

The 1-azabicyclo[m.n.p]alkyl radical having 7 to 11 ring atoms is preferably and by way of example: 1-azabicyclo[3.2.1]octyl (isotropane), 1-azabicyclo[3.3.1]nonyl (isogranatane), 1-azabicyclo[2.2.2]octyl (quinuclidine).

Halogen stands for fluorine, chlorine, bromine and iodine. Fluorine, chlorine and bromine are preferred. Fluorine and chlorine are particularly preferred.

8- to 10-membered heteroaryl stands for an aromatic bicyclic radical having 8 to 10, preferably 9 to 10, ring atoms and up to 5, preferably up to 4, heteroatoms from the series S, O and/or N. The heteroaryl radical may be bonded via a carbon atom or heteroatom. The following may be mentioned by way of example and preferably: indolyl, indazolyl, benzofuranyl, benzothiophenyl, quinolinyl, isoquinolinyl.

If radicals in the compounds of the invention are optionally substituted, the radicals may, unless specified otherwise, be substituted one or more times, identically or differently. Substitution with up to three identical or different substituents is preferred.

Preferred compounds of the general formula (I) are those in which
$R^1$ is 1-azabicyclo[2.2.2]octyl.

Particularly preferred compounds of the general formula (I) are those in which
$R^1$ is 1-azabicyclo[2.2.2]oct-3-yl.

Likewise preferred compounds of the general formula (I) are those in which
A is methylene.

Likewise preferred compounds of the general formula (I) are those in which
$R^2$ is 9- to 10-membered heteroaryl or naphthyl, where the rings are optionally substituted by 1 to 3 radicals selected from the group of hydrogen, halogen, cyano, trifluoromethyl, trifluoromethoxy, nitro, $(C_1-C_4)$-alkyl, $(C_1-C_4)$-alkoxy and $(C_1-C_4)$-alkylthio.

Particularly preferred compounds of the general formula (I) are those in which
$R^2$ is indolyl, benzoimidazolyl, benzotriazolyl, benzothiophenyl, benzofuranyl, quinolinyl, isoquinolyl, benzopyrazinyl, benzopyrimidinyl, benzopyridizanyl or naphthyl, where the rings are optionally, substituted by 1 to 3 radicals selected from the group of hydrogen, halogen, cyano, trifluoromethyl, trifluoromethoxy, nitro, $(C_1-C_4)$-alkyl, $(C_1-C_4)$-alkoxy, $(C_1-C_4)$-alkylthio.

Very particularly preferred compounds of the general formula (I) are those in which
$R^2$ is benzotriazolyl, benzothiophenyl, quinolinyl, benzopyrazinyl or naphthyl, where the rings are optionally substituted by 1 to 3 radicals selected from the group of hydrogen, halogen, cyano, trifluoromethyl, trifluoromethoxy, nitro, $(C_1-C_4)$-alkyl, $(C_1-C_4)$-alkoxy, $(C_1-C_4)$-alkylthio The most preferred compounds of the general formula (I) are those in which
$R^2$ is benzothiophen-2-yl, which is optionally substituted by 1 to 3 radicals selected from the group of hydrogen, halogen, cyano, trifluoromethyl and $C_1-C_4$)-alkyl.

Likewise preferred compounds of the general formula (I) are those in which
$R^3$ is hydrogen or methyl.

Particularly preferred compounds of the general formula (I) are those in which
$R^3$ is hydrogen.

Combinations of two or more of the abovementioned preferred ranges are very particularly preferred.

Likewise very particularly preferred compounds of the general formula (I) are those in which
$R^1$ is 1-azabicyclo[2.2.2]oct-3-yl,
A is methylene,
$R^2$ is benzotriazolyl, benzothiophenyl, quinolinyl, benzopyrazinyl or naphthyl, where the rings are optionally substituted by 1 to 3 radicals selected from the group of hydrogen, halogen, cyano, trifluoromethyl, trifluoromethoxy, nitro, $(C_1-C_4)$-alkyl, $(C_1-C_4)$-alkoxy, $(C_1-C_4)$-alkylthio,
and
$R^3$ is hydrogen.

Likewise very particularly preferred are compounds of the general formula (I), in which
$R^1$ is 1-azabicyclo[2.2.2]oct-3-yl,
A is methylene,
$R^2$ is benzothiophenyl, quinolinyl or naphthyl where the rings are optionally substituted by 1 to 2 radicals selected from the group of hydrogen, fluorine, chlorine, bromine, nitro and
$R^3$ is hydrogen, and the salts, solvates and solvates of the salts thereof.

The invention further relates to a process for preparing the compounds of the formula (I), characterized in that compounds of the general formula (II)

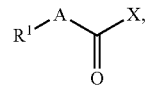

in which
$R^1$ and A have the abovementioned meaning, and
X is hydroxyl or a suitable leaving group,
are reacted with a compound of the general formula (III)

$R^2R^3NH$     (III), in which
$R^2$ and $R^3$ have the abovementioned meaning,
where appropriate in an inert solvent, where appropriate in the presence of a condensing agent and where appropriate in the presence of a base, and the resulting compounds (I) where appropriate are converted with the appropriate (i) solvents and/or (ii) bases or acids into the solvates, salts or solvates of the salts thereof.

If X is a leaving group, chlorine, mesyloxy, isobutyloxycarbonyloxy, pentafluorophenoxy or polymer-bound 4-carboxy-2,3,5,6-tetrafluorophenoxy, in particular chlorine, are preferred.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, acetone, dimethylformamide, dimethylacetamide, dimethyl sulfoxide, acetonitrile or pyridine, with preference for dimethylformamide, methylene chloride, tetrahydrofuran or chloroform.

Condensing agents are, for example, carbodiimides such as, for example, N,N'-diethyl-, N,N'-dipropyl-, N,N'-diisopropyl-, N,N'-dicyclohexylcarbodiimide, N-(3-di-methylaminoisopropyl)-N'-ethylcarbodiimide hydrochloride (EDC), N-cyclohexyl-carbodiimide-N'-propyloxymethylpolystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethyl-amino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexfluorophosphate (HATU) or benzotriazol-1-yloxytris(dimethylamino)phosphonium hexafluorophosphate (BOP), or mixtures thereof.

It may be advantageous where appropriate to use these condensing agents in the presence of an auxiliary nucleophile such as, for example, 1-hydroxybenzotriazole (HOBt).

HATU or the combination of N-(3-dimethylaminoisopropyl)-N'-ethylcarbodiimide hydrochloride (EDC) and 1-hydroxybenzotriazole (HOBt) in dimethylformamide is particularly preferred.

Examples of bases are alkali metal carbonates such as, for example, sodium or potassium carbonate or bicarbonate, or organic bases such as trialkylamines, e.g. triethylamine, or N-methylmorpholine, N-methylpiperidine, 4-dimethylaminopyridine or diisopropylethylamine.

The process of the invention is preferably carried out in a temperature range from room temperature to +50° C. under atmospheric pressure.

The compounds of the general formulae (II) and (III) are known or can be synthesized by known processes from the appropriate precursors (cf., for example, Kato et al. *Chem. Pharm. Bull.* 1995, 43, 1351-1357).

Thus, for example, 1-azabicyclo[2.2.2]oct-3-ylacetic acid can be obtained from quinuclidin-3-one by a Wittig-Horner reaction followed by hydrogenation and ester hydrolysis as shown in the synthesis scheme below.

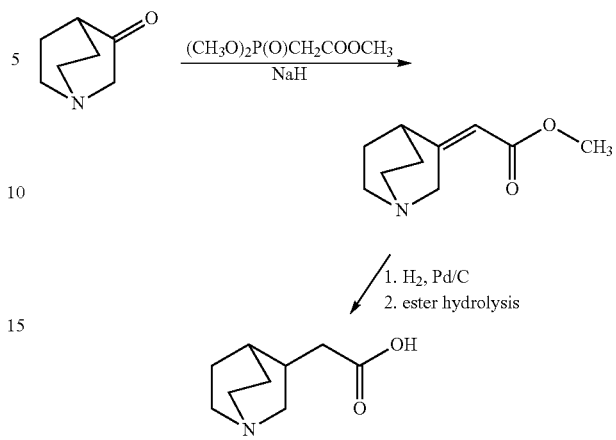

Synthesis scheme

The compounds of the invention of the general formula (I) are suitable for use as medicaments for the treatment and/or prophylaxis of diseases in humans and/or animals.

The compounds of the invention show a valuable range of pharmacological effects which could not have been predicted.

They are notable as ligands, especially agonists, on the α7 nAChR.

The compounds of the invention can, because of their pharmacological properties, be employed alone or in combination with other medicaments for the treatment and/or prevention of cognitive impairments, especially of Alzheimer's disease. Because of their selective effect as α7 nAChR agonists, the compounds of the invention are particularly suitable for improving perception, concentration, learning or memory, especially after cognitive impairments like those occurring for example in situations/diseases/syndromes such as mild cognitive impairment, age-associated learning and memory impairments, age-associated memory loss, vascular dementia, craniocerebral trauma, stroke, dementia occurring after strokes' (post-stroke dementia), post-traumatic craniocerebral trauma, general concentration impairments, concentration impairments in children with learning and memory problems, attention deficit hyperactivity disorder, Alzheimer's disease, vascular dementia, Lewy body dementia, dementia with degeneration of the frontal lobes, including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jacob dementia, HIV dementia, schizophrenia, schizophrenia with dementia or Korsakoff's psychosis.

The compounds of the invention can be employed alone or in combination with other medicaments for the prophylaxis and treatment of acute and/or chronic pain (for a classification, see "Classification of Chronic Pain, Descriptions of Chronic Pain Syndromes and Definitions of Pain Terms", 2nd edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischemia) and trigeminal neuralgia, and other chronic pain such as, for example, lumbago, backache (low back pain) or rheumatic pain. In addition, these active ingredients are also suitable for the therapy of primary acute pain of any origin and of secondary states of pain resulting therefrom, and for the therapy of states of pain which were formerly acute and have become chronic.

The compounds of the invention can be employed alone or in combination with other active ingredients for the treatment of acute or chronic neurodegenerative disorders such as, for example, stroke, craniocerebral trauma, spinal cord injuries, Parkinson's disease, Huntington's disease, Alzheimer's disease, multiple sclerosis, amyotrophic lateral sclerosis (ALS) and Niemann Pick disease.

The in vitro effect of the compounds of the invention can be shown in the following assays:

1. Determination of the Affinity of Test Substances for α7 nAChR by Inhibition of [$^3$H]-Methyllyeaconitine Binding to Rat Brain Membranes The [$^3$H]-methyllycaconitine binding assay is a Modification of the method described by Davies et al. (*Neuropharmacol.* 1999, 38, 679-690).

Rat brain tissue (hippocampus or whole brain) is homogenized in homogenization buffer (10% w/v) [0.32 M sucrose, 1 mM EDTA, 0.1 mM phenylmethylsulfonyl fluoride (PMSF), 0.01% (w/v) NaN$_3$, pH 7.4, 4° C.] at 600 rpm in a glass homogenizer. The homogenate is centrifuged (1000×g, 4° C., 10 min) and the supernatant is removed. The pellet is resuspended (20% w/v) and the suspension is centrifuged (1000×g, 4° C., 10 mM). The two supernatants are combined and centrifuged (15 000×g, 4° C., 30 min). The pellet obtained in this way is referred to as the P2 fraction.

The P2 pellet is washed twice with binding buffer (50 mM Tris-HCl, 1 mM MgCl$_2$, 120 mM NaCl, 5 mM KCl, 2 mM CaCl$_2$, pH 7.4), and centrifuged (15 000×g, 4° C., 30 min).

The P2 membranes are resuspended in binding buffer and incubated in a volume of 250 µl (amount of membrane protein 0.1-0.5 mg) in the presence of 1-5 nM [$^3$H]-methyllycaconitine, 6.1% (w/v) BSA (bovine serum albumin) and various concentrations of the test substance at 21° C. for 2.5 h. The non-specific binding is determined by incubation in the presence of 1 µM α-bungarotoxin or 100 µM nicotine or 10 µM MLA (methyllycaconitine).

The incubation is stopped by adding 4 ml of PBS (20 mM Na$_2$HPO$_4$, 5 mM KH$_2$PO$_4$, 150 mM NaCl, pH 7.4, 4° C.) and filtering through type A/E glass fiber filters (Gelman Sciences) which have previously been placed in 0.3% (v/v) polyethyleneimine (PEI) for 3 h. The filters are washed twice with 4 ml of PBS (4° C.), and the bound radioactivity is determined by scintillation measurement. All the assays are carried out in triplicate. The dissociation constant K$_i$ of the test substance was determined from the IC$_{50}$ of the compounds (concentration of the test substance at which 50% of the ligand bound to the receptor is displaced), the dissociation constant K$_D$ and the concentration L of [$^3$H]-methyllycaconitine using the equation K$_i$=IC$_{50}$/(1+L/K$_D$).

In place of [$^3$H]-methyllycaconitine it is also possible to employ other α7 nAChR-selective radioligands such as, for example, [$^{125}$I]-α-bungarotoxin or nonselective nAChR radioligands together with inhibitors of other nAChRs.

The data on the in vitro effects of the compounds of the invention are shown in Table A:

TABLE A

| Example No. | K$_i$ [nM] |
|---|---|
| 1 | 120 |
| 2 | 200 |
| 3 | 280 |

TABLE A-continued

| Example No. | K$_i$ [nM] |
|---|---|
| 4 | 42 |
| 5 | 170 |

The suitability of the compounds of the invention for the treatment of cognitive impairments can be shown in the following animal models:

2. Object Recognition Test

The object recognition test is a memory test. It measures the ability of rats (and mice) to distinguish between familiar and unfamiliar objects.

The test is carried out as described by Blokland et al., *NeuroReport* 1998, 9, 4205-4208; A. Ennaceur, J. Delacour, *Behav. Brain Res.* 1988, 31, 47-59; A. Ennaceur, K. Meliani, *Psychopharmacology* 1992, 109, 321-330; and Prickaerts et al., *Eur. J. Pharmacol.* 1997, 337, 125-136.

In a first run, a rat is confronted in an otherwise empty observation arena of relatively large size by two identical objects. The rat will investigate, i.e. sniff round and touch, both objects extensively. In a second run, after an interval of 24 hours, the rat is put in the observation arena again. One of the familiar objects has now been replaced by a new, unfamiliar object. If a rat recognizes the familiar object, it will concentrate on investigating the unfamiliar object. However, after 24 hours, a rat has normally forgotten which object it investigated in the first run, and it will therefore inspect both objects to the same extent. Administration of a substance with a learning- and memory-improving effect will lead to a rat recognizing the object seen in the first run 24 hours previously as familiar. It will investigate the new, unfamiliar object in more detail than the familiar one. This memory ability is expressed in a discrimination index. A discrimination index of zero means that the rat investigates both objects, the old and the new, for equal times; that is to say it has not recognized the old object and reacts to both objects as if they were unfamiliar and new. A discrimination index greater than zero means that the rat inspects the new object longer than the old one; that is to say the rat has recognized the old object.

3. Social Recognition Test:

The social recognition test is a test to examine the learning- or memory-improving effect of test substances.

Adult rats housed in groups are placed singly in test cages 30 minutes before the start of the test. Four minutes before the start of the test, the test animal is put in an observation box. After this adaptation time, a juvenile animal is put in with the test animal and the total time for which the adult animal investigates the juvenile animal is measured for 2 minutes (trial 1). All behaviors clearly directed at the young animal are measured, i.e. anogenital inspection, pursuit and grooming, during which the old animal is no further than 1 cm, from the young animal. The juvenile animal is then taken out, and the adult is left in its test cage (for 24-hour retention, the animal is returned to its home cage). The test animal is treated with substance before or after the first test. Depending on the timing of the treatment, the learning or the storage of the information about the young animal can be influenced by the substance. After a fixed period (retention), the test is repeated (trial 2). A larger difference between the investigation times measured in trials 1 and 2 means that the adult animal has remembered the young animal better.

The compounds of the invention of the general formula (I) are suitable for use as medicaments for humans and animals.

The present invention also includes pharmaceutical preparations which, besides inert, nontoxic, pharmaceutically suitable excipients and carriers, contain one or more compounds of the general formula (I), or which consist of one or more compounds of the formula (I), and to processes for producing these preparations.

The compounds of the formula (I) are to be present in these preparations in a concentration of from 0.1 to 99.5% by weight, preferably from 0.5 to 95% by weight, of the complete mixture.

Besides the compounds of the formula (I), the pharmaceutical preparations may also contain other active pharmaceutical ingredients.

The abovementioned pharmaceutical preparations can be produced by known methods in a conventional way, for example using the excipient(s) or carrier(s).

The novel active ingredients can be converted in a known manner into conventional formulations such as tablets, coated tablets, pills, granules, aerosols, syrups, emulsions, suspensions and solutions, using inert, nontoxic, pharmaceutically suitable carriers or solvents. In these cases, the therapeutically active, compound should in each case be present in a concentration of about 0.5 to 90% by weight of the complete mixture, i.e. in amounts which are sufficient to reach the stated dose range.

The formulations are produced for example by extending the active ingredients with solvents and/or carriers, where appropriate with use of emulsifiers and/or dispersants, it being possible for example when water is used as diluent where appropriate to use organic solvents as auxiliary solvents.

Administration takes place in a conventional way, preferably orally, transdermally or parenterally, especially perlingually or intravenously. However, it can also take place by inhalation through the mouth or nose, for example with the aid of a spray, or topically via the skin.

It has generally proved advantageous to administer amounts of about 0.001 to 10 mg/kg, on oral administration preferably about 0.005 to 3 mg/kg, of body weight to achieve effective results.

It may, nevertheless, be necessary where appropriate to deviate from the stated amounts, in particular as a function of the body weight or of the mode of administration, of the individual behavior towards the medicament, the nature of its formulation and the time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

Abbreviations

DCI direct chemical ionization (in MS)
DCM dichloromethane
DMAP 4-N,N-dimethylaminopyridine
DMF N,N-dimethylformamide
DMSO dimethyl sulfoxide
EDC N'-(3-dimethylaminopropyl)-N-ethylcarbodiimide×HCl
ESI electrospray ionization (in MS)
HATU O-(7-Azabenzotriazol-1-yl)-N,N,N',N'-tetramethyluronium hexafluorophosphate
HOBt 1-hydroxy-1H-benzotriazole×H$_2$O
HPLC high pressure, high performance liquid chromatography
LC-MS coupled liquid chromatography-mass spectroscopy
MS mass spectroscopy
NMR nuclear magnetic resonance spectroscopy
PS polystyrene (resin)
RT room temperature
R$_t$ retention time (in HPLC)
THF tetrahydrofuran
HPLC Methods:
Method 1:
Instrument: HP 1100 with DAD detection; column: Kromasil RP-18, 60 mm×2 mm, 3.5 μm; eluent A: 5 ml HClO$_4$/l H$_2$O, eluent acetonitrile; gradient: 0 min 2% B, 0.5 min 2% B, 4.5 min 90% B, 6.5 min 90% B; flow rate: 0.75 ml/min; temperature: 30° C.; detection: UV 210 nm.
Method 2:
Column: Kromasil 100 C-18, 125 mm×3 mm, 5 μm; eluent A: 0.2% HClO$_4$, eluent B: acetonitrile; gradient: 0 min 5% B, 5 min 95% B; flow rate: 1.25 ml/min; temperature: 40° C.; detection: UV 210 nm.

STARTING COMPOUNDS

Example 1A

Quinuclidin-3-one

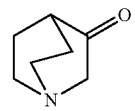

100 g (0.62 mol) of quinuclidin-3-one hydrochloride are suspended in 2 l of methanol. At 0° C., a solution of 33.4 g (0.62 mol) of sodium methoxide in 250 ml of methanol is slowly added dropwise. The mixture is stirred at room temperature for 16 h. The resulting precipitate is filtered off with suction, and the filtrate is concentrated in vacuo. The residue is partitioned between chloroform and water and extracted with chloroform. the combined organic phases are dried over sodium sulfate and concentrated in vacuo. 58.8 g (75.9% of theory) of the title compound are obtained.

MS (DCI): m/z=126 (M+H)$^+$, 143 (M+NH$_4$)$^+$
$^1$H-NMR (300 MHz, CDCl$_3$): δ=3.30 (m, 2H), 3.19-2.86 (m, 4H), 2.46 (m, 1H), 1.99 (m, 4H).

Example 2A

Methyl (2Z)-1-azabicyclo[2.2.2]oct-3-ylideneethanoate hydrochloride

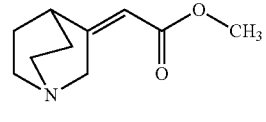

x HCl 25.3 g (0.63 mol) of sodium hydride (as 60% suspension in, mineral oil) are suspended in 480 ml of dimethylformamide. Dropwise addition of a solution of 104.8 g (0.58 mol) of trimethyl phosphonoacetate in 480 ml of dimethylformamide is followed by stirring at room temperature until hydrogen evolution ceases. A solution of 36 g (0.29 mol) of quinuclidin-3-one in 480 ml of dimethylformamide is added dropwise over a period of 40 minutes and then stirred at room temperature for 16 h. The reaction mixture is concentrated in vacuo, and the residue is partitioned between water and ethyl acetate and extracted with ethyl acetate. The combined organic phases are dried over sodium sulfate and concentrated in vacuo. The residue is purified by column chromatography on silica gel (mobile phase: dichloromethane/methanol ammonia=95:5:0.5). The material which has again been concentrated is dissolved in a little dichloromethane and mixed with ethereal HCl. The resulting precipitate is filtered off with suction and washed with diethyl ether. Drying at 35° C. results in 19.53 g (31.2% of theory) of the title compound in the form of white crystals.

HPLC (Kromasil RP-18, 60×2.1 mm; eluent A: $H_2O$+5 ml $HClO_4$/l, eluent B: acetonitrile; gradient: 0-4.5 min 98% A→90% B, 4.5-6.5 min 90% B; flow rate: 0.75 ml/min; temp.: 30° C.; UV detection at 210 nm): $R_t$=2.40 min.

MS (DCI): m/z=182 $(M+H)^+$, 199 $(M+NH_4)^+$, 363 $(2M+H)^+$ $^1$H-NMR (500 MHz, DMSO-$d_6$): δ 11.56 (broad s, 1H), 5.97 (m, 1H), 4.32 (m, 2H), 3.66 (s, 3H), 3.27 (m, 4H), 2.84 (m, 1H), 2.13-1.92 (m, 2H), 1.91-1.69 (m, 2H);

$^{13}$C-NMR (125 MHz, DMSO-$d_6$): δ=165.72, 155.95, 113.08, 53.55, 51.28, 45.29, 30.14, 22.41.

Example 3A

1-Azabicyclo[2.2.2]oct-3-ylacetic acid hydrochloride

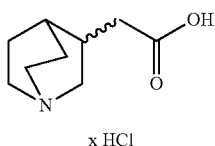 [SMILES: O=C(O)CC1CN2CCC1CC2]

x HCl 13.5 g (62 mmol) of methyl (2Z)-1-azabicyclo[2.2.2]oct-3-ylideneethanoate are dissolved in 200 ml of methanol and, under argon, 1 g of palladium on activated carbon (10%) is added. The reaction mixture is stirred under a hydrogen atmosphere (atmospheric pressure) at room temperature for 16 h. It is filtered through kieselguhr and washed with methanol. The filtrate is mixed with 50 ml of 1 N hydrochloric acid, concentrated in vacuo and dried under high vacuum. The residue is heated in 100 ml of 32% strength hydrochloric acid under reflux for 5 h. The mixture is concentrated in vacuo, codistilled twice with toluene and dried under high vacuum 11.8 g of the product are obtained in a purity of 89% (77% of theory).

HPLC (Kromasil RP-18, 60×2.1 mm; eluent A: $H_2O$+5 ml $HClO_4$/l, eluent B: acetonitrile; gradient: 0-4.5 min 98% A→90% B, 4.5-6.5 min 90% B; flow rate 0.75 ml/min; temp.: 30° C.; UV detection at 210 nm): $R_t$=0.80 min.

MS (DCI): m/z=170 $(M+H)^+$, 339 $(2M+H)^+$ $^1$H-NMR (200 MHz, DMSO-$d_6$): δ=12.32 (broad s, 1H), 10.61 (s, 1H), 3.38 (m, 1H), 3.14 (m, 4H), 2.76 (dd, 1H), 2.67-2.22 (m, 4H), 2.01-1.55 (m, 4H).

Example 4A

6-Methyl bromo-1-benzothiophene-2-carboxylate

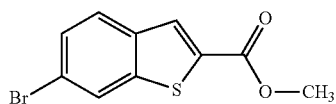

3.76 g (35.5 mmol) of methyl mercaptoacetate are slowly added dropwise to a suspension of 1.93 g (48.3 mmol) of sodium hydride (as 60% suspension in mineral oil) in 65 ml of DMSO at room temperature. After hydrogen evolution ceases, a solution of 6.54 g (32.2 mmol) of 4-bromo-2-fluorobenzaldehyde in 10 ml of DMSO is added. After 10 min, the reaction mixture is stirred into 200 ml of ice-water, and the resulting precipitate is isolated. The Solid is washed twice with water and dried in vacuo at 50° C. 4.06 g (46.4% of theory) of the title compound are obtained.

$^1$H-NMR (200 MHz, DMSO-$d_6$): δ=8.42 (d, 1H), 8.22 (s, 1H), 7.98 (d, 1H), 7.65 (dd, 1H), 3.90 (s, 3H).

HPLC (method 1): $R_t$=5.3 min.

MS (ESIpos): m/z=270 $(M^+)$.

Example 5A

6-Bromo-1-benzothiophene-2-carboxylic acid

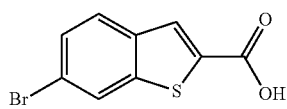 [SMILES: O=C(O)c1cc2ccc(Br)cc2s1]

A solution of 4.0 g (14.8 mmol) of methyl 6-bromo-1-benzothiophene-2-carboxylate in 40 ml of a 1:1 mixture of THF and 2 N potassium hydroxide solution is stirred at room temperature for 2 h. The solvent is removed in vacuo, and the residue is acidified with concentrated hydrochloric acid. The resulting precipitate is filtered off with suction, washed with water and dried in vacuo at 50° C. 3.55 g (93.5% of theory) of the desired product are obtained.

$^1$H-NMR (400 MHz, DMSO-$d_6$): δ=13.48 (broad s, 1H), 8.38 (s, 1H), 8.22 (s, 1H), 7.96 (d, 1H), 7.63 (m, 1H).

HPLC (method 1): $R_t$=4.5 mM.

Example 6A

6-Bromo-1-benzothiophene-2-amine hydrochloride

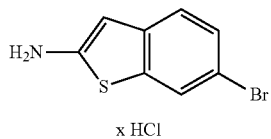 [SMILES: Nc1cc2ccc(Br)cc2s1]

x HCl 0.92 ml (4.28 mmol) of diphenyl phosphorazidate are added to a solution of 1 g (3.89 mmol) of 6-bromo-1-benzothiophene-2-carboxylic acid and 1.35 ml (7.78 mmol) of N,N-diisopropylethylamine in 10 ml of DMF at 0° C. After 2 h at 0° C., the reaction mixture is added to ice-water and neutralized with acetic acid. The resulting precipitate is filtered off with suction and washed with water. The still moist solid is suspended in 5 ml of xylene, added dropwise to 1 ml of boiling tert-butanol and heated under reflux for 3 h. After cooling, the solvent is removed in vacuo. The residue is dissolved in 4 M HCl in dioxane and stirred at room temperature for 1 h. The resulting precipitate is filtered off with suction and dried in vacuo. 294 mg (28.1% of theory) of the title compound are obtained.

HPLC (method 1): $R_t$=5.5 min.

MS (ESIpos): m/z=228 (M+H)$^+$ (free base).

Example 7A

Pentafluorophenyl (1-azabicyclo[2.2.2]oct-3-yl)acetate hydrochloride

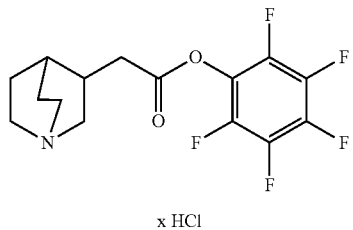 [SMILES: O=C(CC1CN2CCC1CC2)Oc1c(F)c(F)c(F)c(F)c1F]

x HCl 358 mg (1.94 mmol) of pentafluorophenol, 120.5 mg (0.63 mmol) of EDC and 1 drop of N,N-diisopropylethylamine are added to a solution of 100 mg (0.49 mmol) of 1-azabicyclo[2.2.2]oct-3-ylacetic acid hydrochloride in 4 ml of dichloromethane at 0° C. The mixture is stirred at room temperature for 18 h. The contents of the flask are concentrated in vacuo and dried under high vacuum. The resulting crude product is employed without further purification in the following stages.

Example 8A

4-Hydroxy-2,3,5,6-tetrafluorobenzoic acid bound to a polymeric support resin

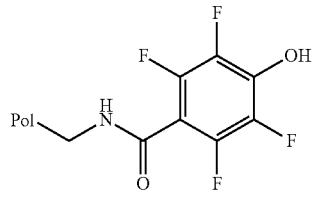

(Pol = polystyrene resin)

51.2 g of polystyrene-aminomethyl resin (loading 1.36 mmol/g, 69.6 mmol; from Argonaut Technologies, USA) are suspended in 700 ml of DMF. 41.6 g (107.8 mmol) of HOBt and 24.1 g (114.8 mmol) of 4-hydroxy-2,3,5,6-tetrafluorobenzoic acid are added. After 15 min, 16.9 ml (107.8 mmol) of N,N'-diisopropylcarbodiimide are added to the reaction mixture while stirring gently, and it is then stirred overnight. It is filtered, and the remaining resin is washed with DMF. The resulting resin is resuspended in 450 ml of DMF, mixed with 8.26 ml (83.5 mmol) piperidine and shaken. After 2, filtration is repeated and the remaining resin is added to a solution of 120 ml of 1 M hydrochloric acid in 500 ml of DMF and shaken for a further 2 h. Renewed filtration is followed by washing with 500 ml each of DMF, THF and DCM. Drying in vacuo at 50° C. results in 77.2 g of the polymer-bound title compound.

Example 9A

4-{2-(1-Azabicyclo[2.2.2]oct-3-yl)acetoxy}-2,3,5,6-tetrafluorobenzoic acid bound to a polymeric support resin

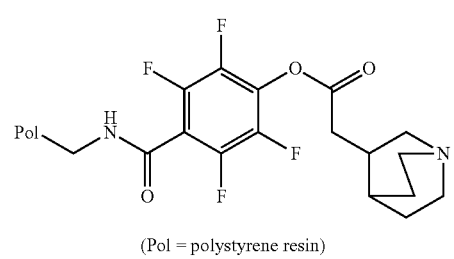

(Pol = polystyrene resin)

2 g of the polymeric support resin from Example 8A (loading about 1.36 mmol/g, 2.72 mmol) are suspended in 20 ml of DMF and shaken with 1.23 g (5.98 mmol) of 1-azabicyclo[2.2.2]oct-3-ylacetic acid hydrochloride and 130 mg (1.09 mmol) of DMAP for 10 min. Then 1.06 ml (6.80 mmol) of N,N'-diisopropylcarbodiimide are added, and the mixture is shaken overnight. The resin is filtered off with suction, washed twice each with 20 ml each of DMF, THF and DCM and dried under high vacuum. 2.318 g of the polymer-bound title compound are obtained.

EXEMPLARY EMBODIMENTS

Example 1

2-(1-Azabicyclo[2.2.2]oct-3-yl)-N-(7-bromo-1-benzothien-2-yl)acetamide hydrochloride

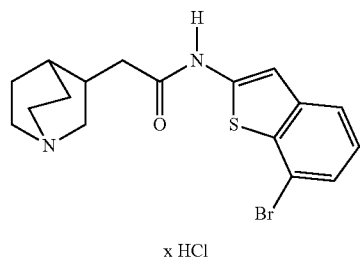 [SMILES: O=C(CC1CN2CCC1CC2)Nc1cc2cccc(Br)c2s1]

x HCl 162.3 mg (0.79 mmol) of the racemic 1-azabicyclo[2.2.2]oct-3-ylacetic acid are introduced together with 120 mg (0.53 mmol) of 3-bromo-1-benzothiophene-2-amine and 300.0 mg (0.79 mmol) of HATU at 0° C. into' DMF. Addition of 102.0 mg (0.79 mmol) of N,N-diisopropylethylamine is followed by stirring for 30 min. A further 204.0 mg (1.58 mmol) of N,N-diisopropylethylamine are added, and the mixture is stirred at RT overnight. Purification takes place by preparative HPLC. The product is dissolved in a little acetonitrile and mixed with an excess of 1 N ethereal HCl. The solvent' is stripped off in vacuo. 12 mg (5% of theory) of the title compound are obtained.

HPLC (Kromasil RP-18, 60×2.1 mm; eluent A: H$_2$O+5 ml HClO$_4$/l, eluent B: acetonitrile; gradient: 0-4.5 min 98%

A→90% B, 4.5-6.5 min 90% B; flow rate: 0.75 ml/min; temp.: 30° C.; UV detection at 210 nm): $R_t$=4.20 min.

MS (ESIpos): m/z=379 (M+H)$^+$ (free base).

Example 2

2-(1-Azabicyclo[2.2.2]oct-3-yl)-N-(6-bromo-1-benzothien-2-yl)acetamide hydrochloride

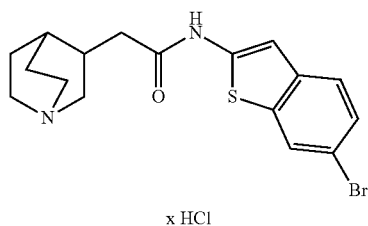 [SMILES: O=C(CC1CN2CCC1CC2)Nc1cc2ccc(Br)cc2s1]

x HCl 89.2 mg (0.24 mmol) of pentafluorophenyl (1-azabicyclo[2.2.2]oct-3-yl)acetate hydrochloride are dissolved in 1 ml of DMF, mixed with 71.2 mg (0.31 mmol) of 6-bromo-1-benzothiophene-2-amine and stirred at room temperature overnight. 1 g of MP-carbonate (polymer-bound carbonate, capacity: 2.5-3.5 mmol/g; from Argonaut Technologies, USA) is added. After 3 h, the polystyrene resin is filtered off and washed with THF. The combined filtrates are concentrated in vacuo, and the crude product is purified by preparative HPLC. The hydrochloride is prepared by mixing the product with a mixture of 1 M hydrochloric acid and acetonitrile and again concentrating. Drying under high vacuum results in 14 mg (14% of theory) of the title compound.

HPLC (method 1): $R_t$=4.2 min.

MS (ESIpos): m/z=379 (M+H)$^+$ (free base).

Example 3

2-(1-Azabicyclo[2.2.2]oct-3-yl)-N-(7-quinolinyl)acetamide hydrochloride

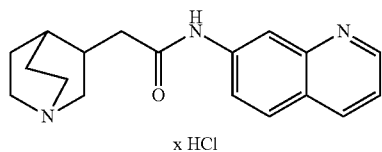 [SMILES: O=C(CC1CN2CCC1CC2)Nc1ccc2cccnc2c1]

x HCl 90.3 mg (0.24 mmol) of pentafluorophenyl (1-azabicyclo[2.2.2]oct-3-yl)acetate hydrochloride are dissolved in 1 ml of DMF, mixed with 51.6 mg (0.36 mmol) of 6-aminoquinoline and stirred at room temperature overnight. 1 g of MP-carbonate (polymer-bound carbonate, capacity: 2.5-3.5 mmol/g; from Argonaut Technologies, USA) is added. After 1 h, the polystyrene resin is filtered off and washed with THF. The combined filtrates are concentrated in vacuo, and the crude product is purified by preparative HPLC. The hydrochloride is prepared by mixing the product with a mixture of 1 M hydrochloric acid and acetonitrile and concentrating again. Drying under high vacuum results in 44 mg (50.2% of theory) of the title compound.

HPLC (method 2): $R_t$=2.8 min.

MS (DCI): m/z=296 (M+H)$^+$ (free base).

Example 4

2-(1-Azabicyclo[2.2.2]oct-3-yl)-N-(2-naphthyl)acetamide hydrochloride

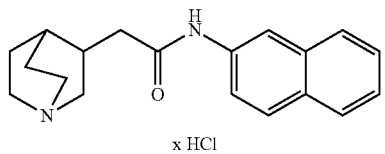 [SMILES: O=C(CC1CN2CCC1CC2)Nc1ccc2ccccc2c1]

x HCl 500 mg of the polymeric support resin from Example 9A (loading about 1.36 mmol/g, 0.68, mmol) are suspended in 5 ml of DMF, mixed with 77.9 mg (0.54 mmol) of 2-aminonaphthylamine and shaken at room temperature for 2 days. The resin is filtered off with suction and washed twice each with THF and DMF. The combined filtrates are concentrated in vacuo. The residue is taken up in methanol, mixed with some palladium on activated carbon (10%) and hydrogenated under atmospheric pressure overnight. The catalyst is filtered off over kieselguhr and washed with methanol. The residue obtained after concentration of the combined methanol filtrates is purified by preparative HPLC. The combined product fractions are mixed with 1 M hydrochloric acid and concentrated. Drying under high vacuum results in 13 mg (4.75% of theory) of the title compound.

HPLC (method 1): $R_t$=3.9 min.

MS (ESIpos): m/z=295 (M+H)$^+$ (free base).

Example 5

2-(1-Azabicyclo[2.2.2]oct-3-yl)-N-(8-nitro-2-naphthyl)acetamide hydrochloride

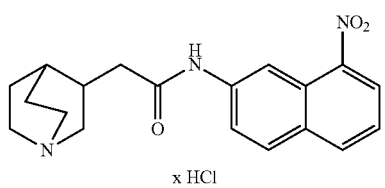 [SMILES: O=C(CC1CN2CCC1CC2)Nc1ccc2cccc([N+](=O)[O-])c2c1]

x HCl 200 mg (0.97 mmol) of 1-azabicyclo[2.2.2]oct-3-ylacetic acid hydrochloride are heated under reflux in 2 ml (27.42 mol) of thionyl chloride for 2 h. The mixture is then freed of excess thionyl chloride in vacuo, and the residue is taken up in 4 ml of DMF. 0.54 ml (3.89 mmol) of triethylamine, 59.4 mg (0.4 mmol) of DMAP and 183.0 mg (0.97 mmol) of 8-nitro-2-naphthylamine are added to this solution. After reaction overnight and purification by preparative HPLC, the resulting product fractions are mixed with 1 M hydrochloric acid and concentrated in vacuo. Recrystallization of the residue from isopropanol and drying under high vacuum result in 59 mg (15% of theory) of the title compound.

HPLC (method 1): $R_t$=3.9 min.

MS (ESIpos): m/z=340 (M+H)$^+$ (free base).

The invention claimed is:
1. A compound selected from the group consisting of:
2-(1-Azabicyclo[2.2.2]oct-3-yl)-N-(7-bromo-1-benzothien-2-yl)acetamide hydrochloride;
2-(1-Azabicyclo[2.2.2]oct-3-yl)-N-(6-bromo-1-benzothien-2-yl)acetamide hydrochloride;
2-(1-Azabicyclo[2.2.2]oct-3-yl)-N-(7-quinolinyl)acetamide hydrochloride;

2-(1-Azabicyclo[2.2.2]oct-3-yl)-N-(2-naphthyl)acetamide hydrochloride, and 2-(1-Azabicyclo[2.2.2]oct-3-yl)-N-(8-nitro-2-naphthyl)acetamide hydrochloride.

2. The compound of claim 1, wherein the compound is 2-(1-Azabicyclo[2.2.2]oct-3-yl)-N-(7-bromo-1-benzothien-2-yl)acetamide hydrochloride.

3. The compound of claim 1, wherein the compound is 2-(1-Azabicyclo[2.2.2]oct-3-yl)-N-(6-bromo-1-benzothien-2-yl)acetamide hydrochloride.

4. The compound of claim 1, wherein the compound is 2-(1-Azabicyclo[2.2.2]oct-3-yl)-N-(7-quinolinyl)acetamide hydrochloride.

5. The compound of claim 1, wherein the compound is 2-(1-Azabicyclo[2.2.2]oct-3-yl)-N-(2-naphthyl)acetamide hydrochloride.

6. The compound of claim 1, wherein the compound is 2-(1-Azabicyclo[2.2.2]oct-3-yl)-N-(8-nitro-2-naphthyl)acetamide hydrochloride.

7. A pharmaceutical composition comprising:
   i) a compound selected from the group consisting of:
      2-(1-Azabicyclo[2.2.2]oct-3-yl)-N-(7-bromo-1-benzothien-2-yl)acetamide hydrochloride;
      2-(1-Azabicyclo[2.2.2]oct-3-yl)-N-(6-bromo-1-benzothien-2-yl)acetamide hydrochloride;
      2-(1-Azabicyclo[2.2.2]oct-3-yl)-N-(7-quinolinyl)acetamide hydrochloride;
      2-(1-Azabicyclo[2.2.2]oct-3-yl)-N-(2-naphthyl)acetamide hydrochloride, and
      2-(1-Azabicyclo[2.2.2]oct-3-yl)-N-(8-nitro-2-naphthyl)acetamide hydrochloride; and
   ii) one or more pharmaceutically acceptable carriers or excipients.

8. The pharmaceutical composition of claim 7, wherein the compound is 2-(1-Azabicyclo[2.2.2]oct-3-yl)-N-(7-bromo-1-benzothien-2-yl)acetamide hydrochloride.

9. The pharmaceutical composition of claim 7, wherein the compound is 2-(1-Azabicyclo[2.2.2]oct-3-yl)-N-(6-bromo-1-benzothien-2-yl)acetamide hydrochloride.

10. The pharmaceutical composition of claim 7, wherein the compound is 2-(1-Azabicyclo[2.2.2]oct-3-yl)-N-(7-quinolinyl)acetamide hydrochloride.

11. The pharmaceutical composition of claim 7, wherein the compound is 2-(1-Azabicyclo[2.2.2]oct-3-yl)-N-(2-naphthyl)acetamide hydrochloride.

12. The pharmaceutical composition of claim 7, wherein the compound is 2-(1-Azabicyclo[2.2.2]oct-3-yl)-N-(8-nitro-2-naphthyl)acetamide hydrochloride.

\* \* \* \* \*